United States Patent [19]
Hilmann et al.

[11] Patent Number: 4,466,442
[45] Date of Patent: Aug. 21, 1984

[54] CARRIER LIQUID SOLUTIONS FOR THE PRODUCTION OF GAS MICROBUBBLES, PREPARATION THEREOF, AND USE THEREOF AS CONTRAST MEDIUM FOR ULTRASONIC DIAGNOSTICS

[75] Inventors: Juergen Hilmann; Rolf-Ruediger Hoffmann; Wolfgang Muetzel; Ingfried Zimmermann, all of Berlin, Fed. Rep. of Germany

[73] Assignee: Schering Aktiengesellschaft, Berlin and Bergkamen, Fed. Rep. of Germany

[21] Appl. No.: 434,034

[22] Filed: Oct. 13, 1982

[30] Foreign Application Priority Data

Oct. 16, 1981 [DE] Fed. Rep. of Germany ....... 3141641

[51] Int. Cl.$^3$ ............................................... A61B 5/00
[52] U.S. Cl. ..................................... 128/653; 128/660
[58] Field of Search .................. 128/653, 669–663; 424/2, 9

[56] References Cited
PUBLICATIONS

Rasor, N. S. and Tickner, E. G., "Ultrasonic Image Enhancement," International Patent Application No. PCT/US80/00502 published Nov. 13, 1980.

Primary Examiner—Kyle L. Howell
Assistant Examiner—Francis J. Jaworski
Attorney, Agent, or Firm—Millen & White

[57] ABSTRACT

The useful lifetime and the amount of microbubbles of a size less than 50 $\mu$m produced by mechanical agitation of an aqueous liquid employed as an ultrasonic contrast medium are increased by employing a liquid containing dissolved therein a tenside which reduces the surface tension of the liquid and a compound which raises the viscosity of the liquid.

26 Claims, No Drawings

CARRIER LIQUID SOLUTIONS FOR THE PRODUCTION OF GAS MICROBUBBLES, PREPARATION THEREOF, AND USE THEREOF AS CONTRAST MEDIUM FOR ULTRASONIC DIAGNOSTICS

BACKGROUND OF THE INVENTION

The invention relates to carrier liquids adapted for the production of microbubbles therein, to the use thereof as contrast medium for ultrasonic diagnostics of fluid-filled vessels or cavities of the human and animal body and to articles of manufacture comprising the carrier liquids.

It is generally known that contrast in ultrasonic diagnostics is enhanced by the presence of gas microbubbles in the liquid, such as blood, flowing through the object to be examined. For this purpose, these microbubbles can be produced outside the subject to be studied and then injected into the bloodstream. This is accomplished, for example, by vigorously shaking a fluid solution, such as a sodium chloride solution, a dye solution or previously withdrawn sample of blood, in order to produce the microbubbles; injecting the resultant microbubble-containing solution; and then conducting the ultrasonic examination as the solution passes through the vessel or cavity.

Thus, Feigenbaum et al., in their article "Identification of Ultrasound Echoes from the Left Ventricle of the Heart Through the Use of Injections of Indocyanine Green" (Circulation, Vol. XLI, April 1970), report on the production of echoes by gas microbubbles in the left ventricle of the heart, as also similarly reported by Gramiak et al. (Radiology 100 : 415–418 (1971). Such methods suffer from the limited concentrations of microbubbles produced and their lifespan after production, both of which profoundly affect the ultrasonic contrast achieved.

Another method for the generation of gas microbubbles of a specific size is described in the report "Non-Invasive Assessment of Pulmonary Hypertension Using the Bubble Ultrasonic Resonance Pressure (BURP) Method" (Report No. HR-62917-1A, April 1977, Division of Lung Diseases, National Heart, Lung and Blood Institute). In this procedure, sugar-encapsulated microbubbles are produced which have to be milled, sieved and separated according to size. The milling procedure is mandatory in order to produce material which can be injected into the body intraarterially without causing hazardous embolism.

U.S. Pat. No. 4,265,251 discloses the production of microgas bubbles with a saccharide envelope, which microbubbles can be generated with a reproducible and highly uniform size distribution, by the use of a relatively expensive and complicated apparatus. The disadvantages of this method are that the solid matrix of microbubbles, shortly prior to use, are openly intermixed with the carrier liquid, whereby sterility and absence of pyrogens are not necessarily ensured. The manufacturing process is also relatively expensive due to the complicated techniques employed. Moreover, the concentration of microbubbles which can be achieved is inherently limited.

In U.S. Pat. No. 4,276,885, a process is described for producing a liquid matrix of microbubbles encapsulated in a gelatinous membrane, using a gelable medium as the carrier for these microbubbles. For storage purposes, the microbubbles can be frozen in place by cooling and then released when required by heating. A disadvantage of this method is the fact that a thus-prepared suspension cannot be sterilized, since the microbubbles are not stable during heat sterilization and are likewise separated or destroyed by sterile filtration. Additionally, there is a risk of anaphylactic reaction with gelatin preparations.

The ultrasonic contrast medium of Application Ser. No. 207,411, filed Nov. 17, 1981, employs a solid microbubble precursor which is used to produce the microbubbles immediately prior to use, e.g., by mixing a particulate solid in a viscous aqueous carrier liquid. This process, like that of U. S. Pat. No. 4,265,251, requires the mixing of the carrier liquid prior to use with a solid in ambient air and the injection into the blood vessel of a mixture containing particulate undissolved solids.

In Abstract No. 770 of Circulation, Vol. 64, published about Oct. 7, 1981, W. J. Bommer et al., report that of the various surfactants, e.g., lecithin, glycerine, etc., which were added to blood and water samples in which microbubbles were produced, presumably in the conventional manner by shaking, those which lowered surface tension of the sample the most achieved the brightest left heart and myocardial perfusion images by contrast videodensitometry. Although we also have found that a surfactant increases the ultrasonic contrast achieved with blood and water samples, a surfactant alone does not achieve the results obtained according to this invention.

The novel ultrasonic contrast medium of this invention avoids the aforedescribed disadvantages of these other methods. We have found that significantly superior imaging is achieved in ultrasonic contrast diagnostics when a liquid vehicle is used to produce the microbubbles which contains both a surfactant (tenside) which lowers substantially the surface tension of the liquid vehicle and a viscosity-raising compound which raises substantially the viscosity of the liquid vehicle.

SUMMARY OF THE INVENTION

In a composition aspect, this invention relates to a combination adapted when microbubbles are formed therein for use as contrast medium for ultrasonic diagnostics, consisting essentially of (a) a solution of an amount from about 0.01% to 10% by weight of at least one tenside in an aqueous intravenously injectable physiologically acceptable aqueous carrier liquid effective to impart a surface tension to the solution of less than 43 dyn/cm; (b) a solution of from about 0.5% to 50% by weight of at least one viscosity-raising compound in an aqueous intravenously injectable physiologically acceptable aqueous carrier liquid, effective to impart a viscosity to the solution of at least 20 mPa·s; and (c) a physiologically acceptable sterile gas for forming microbubbles in a mixture of (a) and (b).

In a method of use aspect, this invention relates, in a method for altering the transmission characteristics of blood to an electromagnetic or elastic wave transmitted therethrough by the steps of forming an amount of microbubbles, effective to substantially alter such transmission characteristics of blood in the area thereof containing the microbubbles, in an intravenously injectable, physiologically acceptable aqueous carrier liquid by mechanically agitating the carrier liquid in the presence of a physiologically acceptable gas, and dispersing the microbubbles in the blood, to the improvement wherein the carrier liquid is substantially free of undissolved solids and contains an amount from about 0.01% to 10% by weight of at least one tenside effective to substantially lower the surface tension of the carrier liquid and an amount from about 0.5% to 50% by weight of at least one viscosity-raising component effective to substantially raise the viscosity of the carrier liquid, and the physiologically acceptable gas is sterile.

In one article of manufacture aspect, this invention relates to a kit for preparing a liquid suspension of microbubbles suitable for use as a contrast medium for ultrasonic diagnostics, comprising:

(a) a first sterile sealed container provided with means for gaining access to the contents thereof with a hypodermic needle under sterile conditions and containing a solution in an intravenously injectable carrier liquid substantially free of undissolved solids, of an amount from 0.02% to 50% by weight of at least one tenside effective to lower the surface tension of the mixture produced when the solution in (a) is mixed with the solution in (b) of less than 43 dyn/cm; and (b) a second sterile sealed container provided with means for gaining access to the contents thereof with a hypodermic needle under sterile conditions and containing and amount of from about 1% to 50% by weight of a solution in an injectable aqueous liquid substantially free of undissolved solids of at least one viscosity-raising compound, effective to impart a viscosity to the mixture produced when the solution in (a) is mixed with the solution in (b) of at least 20 mPa·s; at least one of (a) and (b) also containing a sufficient amount of a sterile physiologically acceptable gas to produce microbubbles in the mixture of (a) and (b) when the mixture is mechanically agitated.

In another article of manufacture aspect, this invention relates to a sealed vial containing a solution, in an intravenously injectable, physiologically acceptable aqueous carrier liquid substantially free of undissolved solids, of an amount from about 0.1% to 10% by weight of at least one tenside effective to substantially lower the surface tension of the carrier liquid and an amount of from about 0.5 to 50% by weight of at least one viscosity-raising compound effective to substantially raise the viscosity of the carrier liquid and a volume of a sterile physiologically acceptable gas sufficient to produce microbubbles in the solution when the solution and gas are mixed by mechanical agitation.

The production of the microbubbles in the contrast medium prior to use can be achieved in a variety of ways, e.g., (1) by transporting at high velocity an intimate mixture of the contrast medium of this invention and air or other physiologically acceptable gas, e.g., by withdrawing into and ejecting from a hypodermic syringe, preferably with several repetitions (pumping) under sterile conditions;

(2) by separately preparing under sterile conditions or subsequently sterilizing (a) a solution of a tenside in a carrier liquid and (b) a solution of a viscosity-raising compound in a carrier liquid, withdrawing the first carrier, and shortly before use injecting the solution (a) into the solution (b), with one of (a) and (b), preferably the latter, being in a sealed sterile container together with a physiologically acceptable gas;

(3) by preparing solutions as in (2), with one of (a) and (b) containing dissolved therein 0.05% to 5% of a physiologically compatible salt of carbonic acid, preferably in a sealed sterile vial with access means, and the other of (a) and (b) containing an amount of physiologically acceptable acid equivalent to the carboxylic acid salt in the other solution, preferably each solution being in a sealed sterile vial with access means, these solutions being mixed together shortly before use under sterile conditions;

(4) storing a sterile mixture of a solution of a tenside and a viscosity-raising compound as defined herein under a sterile atmosphere of a physiologically acceptable gas at superatmospheric pressure, preferably in a sealed vial with access means, and releasing the excess pressure, preferably prior to or after vigorously shaking the solution to mix the gas therewith, immediately prior to use of the solution as an ultrasonic contrast medium.

The mixing of the two liquid mixtures can be conducted by any method which achieves vigorous mingling of the liquid with the physiologically acceptable gas with turbulence, for example by mechanical agitation or by ultrasound or by withdrawing one solution into a hypodermic syringe, preferably the tenside-containing solution, and emptying the syringe into the second mixture with the use of maximum pressure and high efflux velocity and preferably also by subsequent vigorous shaking, under conditions whereby during all mixing steps sterile conditions are ensured. For example, a container is utilized for the mixing step which provides sterile conditions and is sufficiently large that, after receiving the second mixture, still has an adequately large gas space for the subsequent, vigorous shaking. Preferably, multivials (conventional rubberstoppered multidose vials) are used for this purpose having a resilient closure which can be penetrated by a hyperdermic needle and thus permitting injection of one of the solutions therein, subsequent intermixing, and withdrawal of the liquid mixture containing the microbubbles without opening the multivial to the ambient atmosphere.

If desired, the microbubbles can be formed, instead of with sterile air, with another physiologically acceptable sterile gas or mixture of gases, e.g., carbon dioxide, oxygen, nitrogen, noble gases, or mixtures thereof. Sterile air, carbon dioxide, and/or oxygen are the preferred gases. To do so, any air in the mixture of the tenside-containing carrier fluid and/or the viscosity-raising compound-containing carrier fluid is displaced therefrom by gasifying with the desired gas, and the carrier fluids are mixed in one of the aforedescribed ways, e.g., in a multidose vial which has been filled with the desired gas or gas mixture.

If carbon dioxide is desired as the gas, it is also possible to produce the gas in situ during the mixing step by including in or adding to one of the carrier fluids from 1% to 3% by weight of a physiologically acceptable strong acid, such as, for example, hydrochloric acid, tartaric acid, citric acid, or an acidic salt, e.g., of phosphoric acid, and including in or adding, e.g., as a dilute aqueous solution, to the second carrier fluid an equivalent amount of a carbonic acid salt, e.g., alkali or ammonium bicarbonate or sodium bicarbonate.

Microbubbles can also be produced in situ by storing a mixture of the tenside and viscosity-lowering compound in a carrier fluid at superatmospheric pressure over carbon dioxide and releasing the pressure prior to use. The microbubble population is enhanced by vigorous shaking prior to and/or after release of the pressure or by the presence of a nucleating agent in the carrier fluid.

After producing the microbubbles in one of the aboveindicated ways or by an equivalent procedure in the tenside and viscosity-raising compound-containing mixture, it can be employed by intravenous administration as a contrast media for ultrasonic diagnostics in the conventional manner.

This invention provides a contrast medium for ultrasonic diagnostics which is both substantially free of solid particles and whose sterility can be assured. Moreover, the liquid mixtures employed in this invention achieve, by the injection of a very small volume thereof, superior enhancement of ultrasonic contrast. For example, 3 ml. of the suspension described in U.S. Pat. No. 4,276,885 would be required to obtain the ultrasonic contrast enhancement achieved by the intravenous injection of only 0.1 ml. of a contrast agent according to this invention produced, for example, from 1% polyoxyethylene-polyoxypropylene polymer with a molecular weight of 6,800 –8,975 ("Pluronic" F 68) and 4% glucose in water.

A wide variety of both non-ionic and ionic tensides can be employed in the contrast agents of this invention. Examples of suitable non-ionic tensides are lecithins, lecithin fractions and their modification products, polyoxyethylene fatty acid esters, e.g., polyoxyethylene stearates, polyoxyethylene fatty alcohols and polyoxyethylene fatty alcohol ethers, polyoxyethylated sorbitan fatty acid esters, glycerol polyethylene glycol oxystearate, glycerol polyethylene glycol ricinoleate, ethoxylated soybean sterols, ethoxylated castor oils and the hydrogenated derivatives thereof, cholesterol, polyoxyethylene-polyoxypropylene polymers. Polyoxyethylene fatty acid stearates and polyoxyethylene-polyoxypropylene polymers, especially those having a molecular weight of about 6,000 to about 20,000, e.g., about 6,000–9,000, about 13,000, or about 16,000, are preferred.

Examples of suitable ionic tensides are quaternary ammonium bases, sodium lauryl sulfate and sodium dioctyl sulfosuccinate.

The contrast medium solution can contain 0.01–10%, preferably 0.5–5%, of a tenside or a mixture of several tensides, the exact amount depending on the ability thereof to lower the surface tension of the solution and the surface tension value desired for the contrast medium. The contrast medium of this invention has a surface tension of less than 43 dyn/cm, preferably less than 40 dyn/cm.

Examples of viscosity-raising compounds which can be employed are mono- or polysaccharides, e.g., glucose, levulose, galactose, lactose, sorbitol, mannitol, xylitol, saccharose, or dextrans, cyclodextrins, hydroxyethyl amylose and polyols, e.g., glycerol, polyglycols, inulin, and 1,2-propanediol, proteins, proteinaceous materials, amino acids, or blood surrogates, such as, for example, plasma proteins, gelatin, oxypolygelatin and gelatin derivatives or mixtures thereof.

The concentration of these viscosity-raising compounds in the solution can be 0.5–50%, the maximum concentration depending on the solute and the exact amount depending on the viscosity-raising ability of the compound selected and the desired viscosity of the contrast medium. For example, glucose can be used in concentrations of from 0.5–50%, whereas gelatin is preferably employed at a concentration of 0.5–2% and oxypolygelatin is preferably employed at a concentration of 0.5–10%. The contrast medium of this invention has a viscosity of at least 20 mPa·s, preferably at least 24 mPa·s.

It is also possible to employ tensides which also are viscosity-raising compounds, such as, for example, polyoxyethylene-polyoxypropylene polymers, e.g., of a molecular weight of about 4,750–16,250. In this case, the concentration of the tensides with a viscosity-raising effect is 1% to 20%, preferably 3% to 10%. The tenside or tenside mixture is preferably dissolved in a carrier liquid in the presence of the viscosity-raising compound or mixture of compounds.

The carrier liquid or liquids of this invention are substantially free of undissolved solids. The tenside and viscosity-raising compound are dissolved therein as a true solution or a colloidal dispersion. The carrier liquid is preferably water. Physiologically acceptable aqueous solutions such as, for example, physiological electrolyte solutions, e.g., physiological saline solutions, Ringer's solution, or aqueous solutions of sodium chloride, calcium chloride, sodium bicarbonate, sodium citrate, sodium acetate or sodium tartrate, or salt solutions as customarily employed as infusion solutions, can also be employed, as can aqueous solutions containing a physiologically acceptable mono- or polyhydric alcohol, e.g., ethanol, n-butanol, ethylene glycol, polyvinylpyrrolidone.

Contemplated equivalents of the aqueous carrier liquids of this invention are physiologically acceptable intravenously injectable non-aqueous, i.e., anhydrous or substantially anhydrous carrier liquids, e.g., alcohols, glycols and polyglycols, the synthetic perfluoronated hydrocarbons and other types of blood extenders. Some of these non-aqueous carrier liquids are relatively toxic but because such a little amount thereof is employed in ultrasonic contrast diagnostics, e.g., as little as 0.5 cc, they nevertheless fall within the definition of physiologically acceptable intravenously injectable liquids as used herein.

Articles of manufacture adapted for carrying out the method of this invention comprise, in one aspect, a sealed container, e.g., a conventional multidose vial, e.g., of 10 to 50 cc, preferably 15 to 25 cc volume, sealed with access means, e.g., a resilient elastomeric stopper for gaining access to the contents thereof under sterile conditions, and containing a selected volume, e.g., 0.5 to 25 cc, preferably 1 to 15 cc, of a sterile carrier liquid solution of this invention, under an atmosphere of a sterile physiologically acceptable gas, of a tenside and a viscosity-raising compound. In another article of manufacture aspect there is provided as a kit, one such container containing a carrier liquid as described above or one containing only the viscosity-raising compound, over an atmosphere of a sterile physiologically acceptable gas, in which the microbubbles are formed, another container containing a sterile aqueous carrier liquid as defined hereinbefore, preferably one containing only a tenside, in the absence of a physiologically acceptable gas, e.g., a conventional glass vial with breakable neck to permit access to the contents with a hypodermic syringe, or in the presence of such a gas, e.g., a single dose vial with resilient elastomeric stopper as defined above.

In carrying out the method of this invention, microbubbles are introduced into the selected carrier liquid, e.g., by mechanical agitation, to produce a suspension of microbubbles in the carrier liquid containing both a tenside and a viscosity-raising compound as defined herein. Such a carrier liquid can be present prior to forming the microbubbles, e.g., in a conventional multidose vial with resilient closure under an atmosphere of a physiologically acceptable gas as described above, or can be formed simultaneously with forming the microbubbles, e.g., employing a kit as described above in which one of the containers contains a solution of a tenside and the other contains a solution of a viscosity-raising compound, with one, preferably the latter, or both being under an atmosphere of the selected physiologically acceptable gas.

Usually the mechanical agitation employed to produce microbubbles of this invention also concurrently produces macrobubbles which collect as a foam on the surface of the carrier liquid. The injection of macrobubbles can readily be avoided by forming the microbubbles in a larger volume of carrier liquid than needed to conduct an ultrasonic contrast diagnosis and withdrawing the amount needed for the diagnosis from below the surface of the carrier liquid, e.g., with a hypodermic needle. The carrier liquid is injected intravenously in the conventional manner within 5 minutes, preferably within 2 minutes after forming the microbubbles therein.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the examples and in the description hereinbefore, percentages are by weight.

EXAMPLE 1

Employing a hypodermic syringe, 2 ml of a 20% sterile aqueous "Pluronic" F 68 solution is withdrawn from and injected with maximally high efflux velocity into 8 ml of a sterile aqueous 5% glucose solution present in a sterile 25 ml multivial (a standard glass vial sealed with a rubber stopper) under a sterile air atmosphere. The thus-prepared solution contains 4% "Pluronic" F 68 and 4% glucose. The mixture is then vigorously shaken. A layer of a foam of macrobubbles and a liquid layer containing microbubbles is produced. The size distribution of the microbubbles in the liquid layer is measured with a modified Cilas Granulometer. Two minutes after their production, 50% of the microbubbles in the liquid layer had a diameter of $<50$ μm and the remainder up to about 100 μm.

EXAMPLE 2

Analogously to Example 1, but using a 10% aqueous and sterile "Pluronic" F 68 solution, a suspension of microbubbles in 2% "Pluronic" F 68 and 4% glucose is obtained. The size distribution of the gas microbubbles in the liquid layer, determined by the Cilas Granulometer, is 50% $<45$ μm, the remainder, up to 100 μm.

EXAMPLE 3

Analogously to Example 1, but using a 5% sterile aqueous "Pluronic" F 68 solution after mixing, a microbubble suspension in 1% "Pluronic" F 68 and 4% glucose is obtained. The microbubble size in the liquid layer, as determined with the Cilas Granulometer, 50% $<55$ μm, remainder, up to 100 μm.

EXAMPLE 4

Using a hypodermic syringe, 2 ml of an aqueous sterile 10% "Pluronic" F 127 solution is withdrawn and injected with a maximum high efflux velocity into a 25 ml multivial containing 8 ml of a sterile physiological sodium chloride solution under sterile air atmosphere to produce a microbubble suspension in 2% "Pluronic" F 127 and 0.9% sodium chloride. The mixture is then vigorously shaken to enhance the microbubbles. The "Pluronic" F 127 employed at this concentration is both a tenside and viscosity raising compound. The average microbubble size in the liquid layer, determined with a modified Cilas Granulometer, 2 minutes after preparation is 50% $<45$ μm.

EXAMPLE 5

Using a hypodermic syringe, 2 ml is withdrawn from a sterile aqueous 5% "Pluronic" F 68 solution, from which dissolved air therein previously had been displaced by argon. This amount is injected with maximum high efflux speed into a sterile 25 ml multivial containing 8 ml of a sterile aqueous 6% dextran 40 solution, from which the dissolved air had likewise been displaced with argon, under an argon atmosphere to obtain a microbubble-containing solution of 1% "Pluronic" F 68 and 4.8% dextran 40. The mixture is then vigorously shaken to enchance microbubble population. The size distribution of the argon gas microbubbles in the liquid layer, determined 2 minutes after production with the Cilas Granulometer 715, was 50% $<55$ μm.

EXAMPLE 6

Analogously to Example 5, but using helium instead of argon, after the mixing step a helium gas microbubble suspension in 1% "Pluronic " F 68 and 4.8% dextran 40 is obtained. The size distribution of the helium gas microbubbles in the liquid layer 2 minutes after preparation is 50% $<65$ μm.

EXAMPLE 7

Analogously to Example 5, but using oxygen in place of argon, after the mixing step, an oxygen gas microbubble suspension in 1% "Pluronic" F 68 and 4.8% dextran 40 is obtained. The size distribution of the oxygen gas microbubbles in the liquid layer 2 minutes after preparation is 50% $<60$ μm.

EXAMPLE 8

Using a hypodermic syringe, 2 ml of a sterile 5% "Pluronic" F 68 solution in 0.4N tartaric acid is withdrawn and then injected with a maximum high efflux velocity into a sterile 25 ml multivial containing 8 ml of a sterile 5% glucose solution in 01.N sodium bicarbonate, under sterile air. The mixture is vigorously shaken to obtain a microbubble suspension in 1% "Pluronic" F 68 and 4% glucose. The size distribution of the microbubbles in the liquid layer, measured with a modified Cilas Granulometer 2 minutes after production, is 50% $<45$ μm.

EXAMPLE 9

Analogously to Example 1, but using a 2% sterile aqueous "Pluronic" F 68 solution and a 12.5% sterile aqueous glucose solution, a microbubble suspension in an 0.4% "Pluronic" F 68 and 2.5% glucose solution is obtained, the diameter of which 2 minutes after mixing is 50% $<55$ μm.

EXAMPLE 10

Ten milliliter portions of a sterile aqueous solution of 10% by weight of lactose and 0.5% by weight of "Pluronic" F 68 are sealed under sterile conditions in conventional 25 ml multivials containing ambient air. Upon vigorous shaking and/or repeatedly withdrawing the solution from and injecting it into the vial, a stable (at least 2 minutes) suspension of microbubbles in the solution is produced which is suitable for use as the contrast medium for ultrasonic diagnostics. This solution presently is the preferred embodiment of the carrier liquids of this invention.

EXAMPLE 11

0.3 ml of a microbubble suspension produced by vigorously mixing together in a sterile air atmosphere, 2 ml of a 5% aqueous sterile "Pluronic" F 68 solution and 8 ml of a 5% aqueous sterile glucose solution was utilized for ultrasonic contrast imaging of the right heart ventricle in dogs (beagles body weight 17.2 kg, 2.5 years of age, male, closed thorax). In the mixing step, the "Pluronic" F 68 solution was drawn into a hypodermic syringe and then injected with high efflux into a multidose vial containing the glucose solution and sterile air. The mixed solutions were thereafter shaken to produce a foam of macrobubbles on top of a microbubble-containing layer of 1% "Pluronic" F 68 and 4% glucose solution. The microbubbles in the liquid layer was measured 2 minutes after mixing by means of a Cilas Granulometer 715 and found to be $<35$ $\mu$m for 50% of the gas bubbles with the remainder of various sizes up to about 100 $\mu$m. Imaging and recording of the ultrasonic echoes as well as their diagnostic evaluation takes place conventionally and is described, for example, in U.S. Pat. No. 4,276,885 and by H. L. Wyatt et al. in Circulation 60:1104f (1979).

Each of the foregoing microbubble-containing carrier liquids produce superior visualization when employed as an ultrasonic contrast medium, than blood or water samples containing only a viscosity-raising compound or only a surfactant or a lesser amount of only a compound which is both a surfactant and a viscosity-raising compound. The tenside ensures that a large population of microbubbles with diameters less than 50 $\mu$m will be produced and the viscosity-raising agent ensures the stability and an acceptable lifetime of that population.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A combination adapted when microbubbles are formed therein for use as contrast medium for ultrasonic diagnostics, consisting essentially of
   (a) an amount from about 0.01% to 10% by weight of at least one tenside, as a solution in an aqueous intravenously injectable physiologically acceptable aqueous carrier liquid, effective to impart a surface tension to the solution of less than 43 dyn/cm;
   (b) an amount from about 0.5% to 50% by weight of at least one viscosity-raising compound, as a solution in an aqueous intravenously injectable physiologically acceptable aqueous carrier liquid, effective to impart a viscosity to the solution of at least 20 mPa·s; wherein (a) and (b) are present in the combination as a single solution or as separate solutions which, when mixed, form the single solution; and
   (c) a physiologically acceptable sterile gas for forming microbubbles in a mixture of (a) and (b).

2. A combination according to claim 1 wherein (a) and (b) are present in the combination as a single solution.

3. A combination according to claim 1 wherein (a) and (b) are present in the combination as separate solutions.

4. A combination according to claim 2, produced by mixing together separate solutions of (a) and (b) to form the single solution and the physiologically acceptable sterile gas and wherein one of the separate solutions contains 0.05–5% by weight of a physiologically acceptable salt of carbonic acid, and the other contains an amount of physiologically acceptable acid equivalent to and reactive with the carbonic acid salt.

5. A combination according to claim 1 wherein the tenside of (a) is non-ionic.

6. A combination according to claim 5 wherein the nonionic tenside contains a polyoxyethylene-polyoxypropylene polymer.

7. A combination according to claim 6 wherein the polyoxyethylene-polyoxypropylene polymer has a molecular weight of about 6,000 to 9,000, about 13,000 or about 16,000.

8. A combination according to claim 5 wherein the nonionic tenside is a polyoxyethylene fatty acid ester or a polyoxyethylene stearate.

9. A combination according to claim 1 wherein the tenside is an ionic tenside.

10. A combination according to claim 9 wherein the ionic tenside is sodium lauryl sulfate or sodium dioctylsulfosuccinate.

11. A combination according to claim 10 wherein the carrier liquid is water, a physiological saline solution or Ringer's solution.

12. A combination according to claim 1 wherein the viscosity-raising compound is gelatin or oxypolygelatin.

13. A combination according to claim 1 wherein the viscosity-raising compound is lactose or glucose.

14. A combination according to claim 1 wherein the physiologically acceptable gas is air, carbon dioxide, oxygen, nitrogen, a noble gas or mixture thereof.

15. A combination according to claim 14 wherein the physiologically acceptable gas is air.

16. A combination according to claim 14 wherein the physiologically acceptable gas is carbon dioxide.

17. A combination according to claim 1 wherein (a) is a 1% solution in water of polyoxyethylene-polypropylene polymer having a molecular weight of about 6,000 to 9,000 and (b) is about a 1% solution of gelatin in water.

18. In a method for altering the transmission characteristics of blood to an electromagnetic or elastic wave transmitted therethrough by the steps of forming an amount of microbubbles effective to substantially alter such transmission characteristics of blood in the area thereof containing the microbubbles in an intravenously injectable physiologically acceptable aqueous carrier liquid by mechanically agitating the carrier liquid in the presence of a physiologically acceptable gas, and dispersing the microbubble-containing carrier liquid in the blood, the improvement wherein the carrier liquid is substantially free of undissolved solids, has a surface tension of less than 43 dyn/cm and a viscosity of at least 20 mPa·s, and the physiologically acceptable gas is sterile.

19. A method according to claim 18 wherein at least a portion of the microbubbles are formed by injecting a solution of the tenside in an intravenously injectable, physiologically acceptable carrier liquid into a solution of the viscosity-raising compound in an intravenously injectable, physiologically acceptable carrier liquid under an atmosphere of the physiologically acceptable gas.

20. A method according to claim 19 wherein the thusproduced mixture of microbubble-containing solution of tenside and viscosity-raising compound is mechanically agitated under an atmosphere of the physiologically acceptable gas prior to dispersing the mixture in the blood.

21. A method according to claim 18 wherein at least a portion of the microbubbles are formed by injecting a portion of the solution of the tenside and viscosity-raising compound into another portion of the solution, under an atmosphere of the physiologically acceptable gas.

22. A method according to claim 21 wherein the thusproduced mixture of microbubble-containing solution of tenside and viscosity-raising compound is mechanically agitated under an atmosphere of the physiologically acceptable gas prior to dispersing the mixture in the blood.

23. A method according to claim 18 wherein the carrier liquid is produced immediately prior to being mechanically agitated with the physiologically acceptable gas by mixing (a) a solution of an amount from about 0.01% to 10% by weight of at least one tenside in an aqueous intravenously injectable physiologically acceptable aqueous carrier liquid, effective to impart a surface tension to the solution of less than 43 dyn/cm, with (b) a solution of an amount from about 0.5% to 50% by weight of at least one viscosity-raising compound in an aqueous intravenously injectable physiologically acceptable aqueous carrier liquid, effective to impart a viscosity to the solution of at least 20 mPa·s.

24. A kit for preparing a liquid suspension of microbubbles suitable for use as a contrast medium for ultrasonic diagnostics, comprising (a) a first sterile sealed container provided with a means for gaining access to the contents thereof with a hypodermic needle under sterile conditions and containing a solution in an intravenously injectable carrier liquid substantially free of undissolved solids, of an amount from 0.02% to 50% by weight of at least one tenside effective to lower the surface tension of the mixture produced when the solution in (a) is mixed with the solution in (b) to less than 43 dyn/cm; and (b) a second sterile sealed container provided with means for gaining access to the contents thereof with a hypodermic needle under sterile conditions and containing an amount of from about 1% to 50% by weight of a solution in an injectable aqueous liquid substantially free of undissolved solids of at least one viscosity-raising compound, effective to impart a viscosity to the mixture produced when the solution in (a) is mixed with the solution in (b) of at least 20 mPa·s; at least one of (a) and (b) also containing a sufficient amount of a sterile physiologically acceptable gas to produce microbubbles in the mixture of the solution in (a) and (b) when the mixture is mechanically agitated.

25. A kit according to claim 24 wherein (b) contains a sufficient amount of a physiologically acceptable gas to produce the microbubbles.

26. A sealed vial containing a solution, in an intravenously injectable, physiologically acceptable aqueous carrier liquid substantially free of undissolved solids, of an amount from about 0.1% to 10% by weight of at least one tenside effective to substantially lower the surface tension of the carrier liquid and an amount of from about 0.5 to 50% by weight of at least one viscosity-raising compound effective to substantially raise the viscosity of the carrier liquid and a volume of a sterile physiologically acceptable gas sufficient to produce microbubbles in the solution when the solution and gas are mixed by mechanical agitation.

* * * * *